(12) United States Patent
Takenaka (10) Patent No.: US 9,513,212 B2
(45) Date of Patent: Dec. 6, 2016

(54) PHOTOCONDUCTIVE ANTENNA, CAMERA, IMAGING DEVICE, AND MEASUREMENT DEVICE

(71) Applicant: SEIKO EPSON CORPORATION, Tokyo (JP)

(72) Inventor: Satoshi Takenaka, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/629,130

(22) Filed: Feb. 23, 2015

(65) Prior Publication Data

US 2015/0241005 A1  Aug. 27, 2015

(30) Foreign Application Priority Data

Feb. 24, 2014 (JP) ................... 2014-032798

(51) Int. Cl.
 *G01J 5/08* (2006.01)
 *G01N 21/3581* (2014.01)
(52) U.S. Cl.
 CPC .................. *G01N 21/3581* (2013.01)
(58) Field of Classification Search
 CPC ...................... G01J 5/02; H04N 5/33
 See application file for complete search history.

(56) References Cited

U.S. PATENT DOCUMENTS

| | | | |
|---|---|---|---|
| 6,738,397 B2 | 5/2004 | Yamamoto et al. | |
| 7,659,137 B2 | 2/2010 | Kasai et al. | |
| 8,093,560 B2 | 1/2012 | Kuroyanagi et al. | |
| 2010/0052083 A1* | 3/2010 | Kasai | 257/431 |
| 2010/0276594 A1* | 11/2010 | Rafailov et al. | 250/338.4 |
| 2011/0127431 A1 | 6/2011 | Paek | |
| 2012/0326036 A1* | 12/2012 | Tomioka | 250/338.1 |
| 2014/0240510 A1 | 8/2014 | Takenaka | |

FOREIGN PATENT DOCUMENTS

| | | |
|---|---|---|
| JP | 11-330504 A | 11/1999 |
| JP | 2003-015175 A | 1/2003 |
| JP | 2004-207288 A | 7/2004 |
| JP | 2005-026347 A | 1/2005 |
| JP | 04785392 B | 3/2005 |
| JP | 2006-145372 A | 7/2006 |

(Continued)

OTHER PUBLICATIONS

"Laser Studies" academic journal of the Laser Society of Japan, vol. 26, No. 7, 1998.

*Primary Examiner* — David Porta
*Assistant Examiner* — Hugh H Maupin
(74) *Attorney, Agent, or Firm* — Maschoff Brennan (57) ABSTRACT

A photoconductive antenna that generates a terahertz wave by irradiation with a light pulse, includes: a carrier generation layer that has carriers formed therein by irradiation with the light pulse, and is constituted by a semi-insulating substrate; an insulating layer, located on the carrier generation layer, which is capable of transmitting the light pulse; and a first electrode and a second electrode, located above the carrier generation layer, which apply a voltage to the carrier generation layer, wherein the insulating layer is provided on a region which is irradiated with the light pulse between the first electrode and the second electrode in a plan view.

20 Claims, 7 Drawing Sheets

(56) References Cited

FOREIGN PATENT DOCUMENTS

| | | | |
|---|---|---|---|
| JP | 2006-313803 | A | 11/2006 |
| JP | 2007-278740 | A | 10/2007 |
| JP | 2009-124437 | A | 6/2009 |
| JP | 2010-187007 | A | 8/2010 |
| JP | 2011-119642 | A | 6/2011 |
| JP | 2014-165413 | A | 9/2014 |

* cited by examiner

PHOTOCONDUCTIVE ANTENNA, CAMERA, IMAGING DEVICE, AND MEASUREMENT DEVICE

BACKGROUND

1. Technical Field

The present invention relates to a photoconductive antenna, a camera, an imaging device, and a measurement device.

2. Related Art

In recent years, terahertz waves which are electromagnetic waves having a frequency equal to or greater than 100 GHz and equal to or less than 30 THz have attracted attention. The terahertz waves can be used in, for example, various types of measurement such as imaging and spectroscopic measurement, non-destructive tests, and the like.

Terahertz wave generation devices that generate such terahertz waves include, for example, a light pulse generation device that generates a light pulse having a pulse width of approximately subpicoseconds (several hundred femtoseconds), and a photoconductive antenna that generates a terahertz wave by irradiation with the light pulse generated in the light pulse generation device.

For example, JP-A-2009-124437 discloses a photoconductive antenna including a semi-insulating GaAs substrate, a GaAs (LT-GaAs) layer formed on the semi-insulating GaAs substrate by a low-temperature MBE (molecular beam epitaxy) method, and a pair of electrodes formed on the LT-GaAs layer. Further, JP-A-2009-124437 discloses that free carriers excited in the LT-GaAs layer are accelerated by an electric field caused by a bias voltage, whereby a current flows, and a terahertz wave is generated due to a change in this current.

The intensity of the terahertz wave which is generated in the above-mentioned photoconductive antenna is preferably large, whereby it is possible to realize a camera, an imaging device, and a measurement device having, for example, high detection sensitivity.

It is known that the intensity of a terahertz wave which is generated in a photoconductive antenna is dependent on the carrier mobility of a layer through which carriers transfer (travel) in the photoconductive antenna. That is, as the carrier mobility of the layer becomes larger, the intensity of the terahertz wave which is generated in the photoconductive antenna becomes larger.

In the photoconductive antenna disclosed in JP-A-2009-124437, since the carrier mobility (electron mobility) of the LT-GaAs layer has a small rate of 100 $cm^2/Vs$ to 150 $cm^2/Vs$, the time variation of a photocurrent decreases, and thus it may not be possible to generate a terahertz wave having a large intensity. For this reason, it may not be possible to realize a camera, an imaging device, and a measurement device which have high detection sensitivity.

SUMMARY

An advantage of some aspects of the invention is to provide a photoconductive antenna which is capable of enhancing carrier mobility more than in the related art, and generating a terahertz wave having a large intensity. Another advantage of some aspects of the invention is to provide a camera, an imaging device, and a measurement device which include the aforementioned photoconductive antenna.

An aspect of the invention is directed to a photoconductive antenna that generates a terahertz wave by irradiation with a light pulse, including: a carrier generation layer that has carriers formed therein by irradiation with the light pulse, and is constituted by a semi-insulating substrate; an insulating layer, located on the carrier generation layer, which is capable of transmitting the light pulse; and a first electrode and a second electrode, located above the carrier generation layer, which apply a voltage to the carrier generation layer, wherein the insulating layer is provided on a region which is irradiated with the light pulse between the first electrode and the second electrode in a plan view.

In such a photoconductive antenna, it is possible to further enhance carrier mobility than in a case where the carrier generation layer is formed of an LT-GaAs layer, and to generate (radiate) a terahertz wave having a large intensity. Therefore, in such a photoconductive antenna, it is possible to achieve an increase in power.

Meanwhile, in the disclosure according to the invention, when the wording "above" is used in, for example, the phrase "form another specific thing (hereinafter, referred to as "B") "above" a specific thing (hereinafter, referred to as "A")" or the like, a case where B is formed directly on A and a case where B is formed on A through another thing are assumed to be included, and the wording "above" is used.

In the photoconductive antenna according to the aspect of the invention, the first electrode and the second electrode may be provided on the insulating layer.

In such a photoconductive antenna, it is possible to suppress a flow of a leakage current between the first electrode and the second electrode, and to improve a breakdown voltage.

In the photoconductive antenna according to the aspect of the invention, the insulating layer may terminate a dangling bond located on the surface of the carrier generation layer.

In such a photoconductive antenna, it is possible to prevent the carriers traveling along the vicinity of the surface of the carrier generation layer from being trapped by the dangling bond. Therefore, in such a photoconductive antenna, it is possible to achieve an increase in power.

In the photoconductive antenna according to the aspect of the invention, the insulating layer may be formed of any of silicon oxide, silicon nitride, or a compound of aluminum gallium arsenide and oxygen.

In such a photoconductive antenna, atoms constituting the insulating layer can be bonded to atoms constituting the surface of the carrier generation layer by the dangling bond which is not involved in bonding in the carrier generation layer. Therefore, in such a photoconductive antenna, it is possible to prevent the carriers traveling along the vicinity of the surface of the carrier generation layer from being trapped by the dangling bond. Therefore, in such a photoconductive antenna, it is possible to achieve an increase in power.

Another aspect of the invention is directed to a terahertz wave generation device including: a light pulse generation device that generates a light pulse; and the photoconductive antenna according to the aspect of the invention which generates the terahertz wave by irradiation with the light pulse.

In such a terahertz wave generation device, since the photoconductive antenna is included, it is possible to achieve an increase in power.

Still another aspect of the invention is directed to a camera including: a light pulse generation device that generates a light pulse; the photoconductive antenna according to the aspect of the invention which generates the terahertz wave by irradiation with the light pulse; a terahertz wave detection portion that detects the terahertz wave emitted from the photoconductive antenna and passing through an object or the terahertz wave reflected from the object; and a storage portion that stores detection results of the terahertz wave detection portion.

In such a camera, since the photoconductive antenna according to the above aspects is included, it is possible to have high detection sensitivity.

Yet another aspect of the invention is directed to an imaging device including: a light pulse generation device that generates a light pulse; the photoconductive antenna according to the aspect of the invention which generates the terahertz wave by irradiation with the light pulse; a terahertz wave detection portion that detects the terahertz wave emitted from the photoconductive antenna and passing through an object or the terahertz wave reflected from the object; and an image forming portion that generates an image of the object on the basis of detection results of the terahertz wave detection portion.

In such an imaging device, since the photoconductive antenna according to the above aspects is included, it is possible to have high detection sensitivity.

Still yet another aspect of the invention is directed to a measurement device including: a light pulse generation device that generates a light pulse; the photoconductive antenna according to the aspect of the invention which generates the terahertz wave by irradiation with the light pulse; a terahertz wave detection portion that detects the terahertz wave emitted from the photoconductive antenna and passing through an object or the terahertz wave reflected from the object; and a measurement portion that measures the object on the basis of detection results of the terahertz wave detection portion.

In such a measurement device, since the photoconductive antenna according to the above aspects is included, it is possible to have high detection sensitivity.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail with reference to the accompanying drawings. Meanwhile, the embodiments described below are not unduly limited to the disclosure of the invention described in the appended claims. In addition, all the configurations described below are not necessarily the essential components of the invention.

1. Photoconductive Antenna

Figure 1:
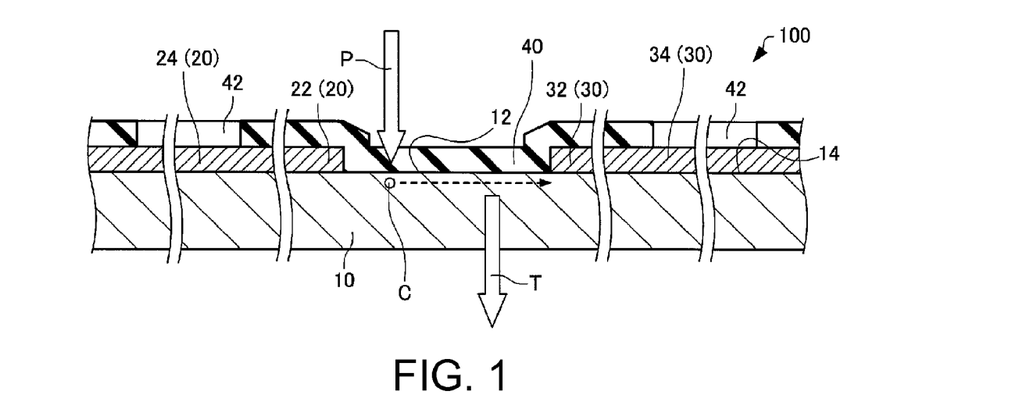
FIG. 1 is a cross-sectional view schematically illustrating a photoconductive antenna according to the present embodiment.
Figure 2:
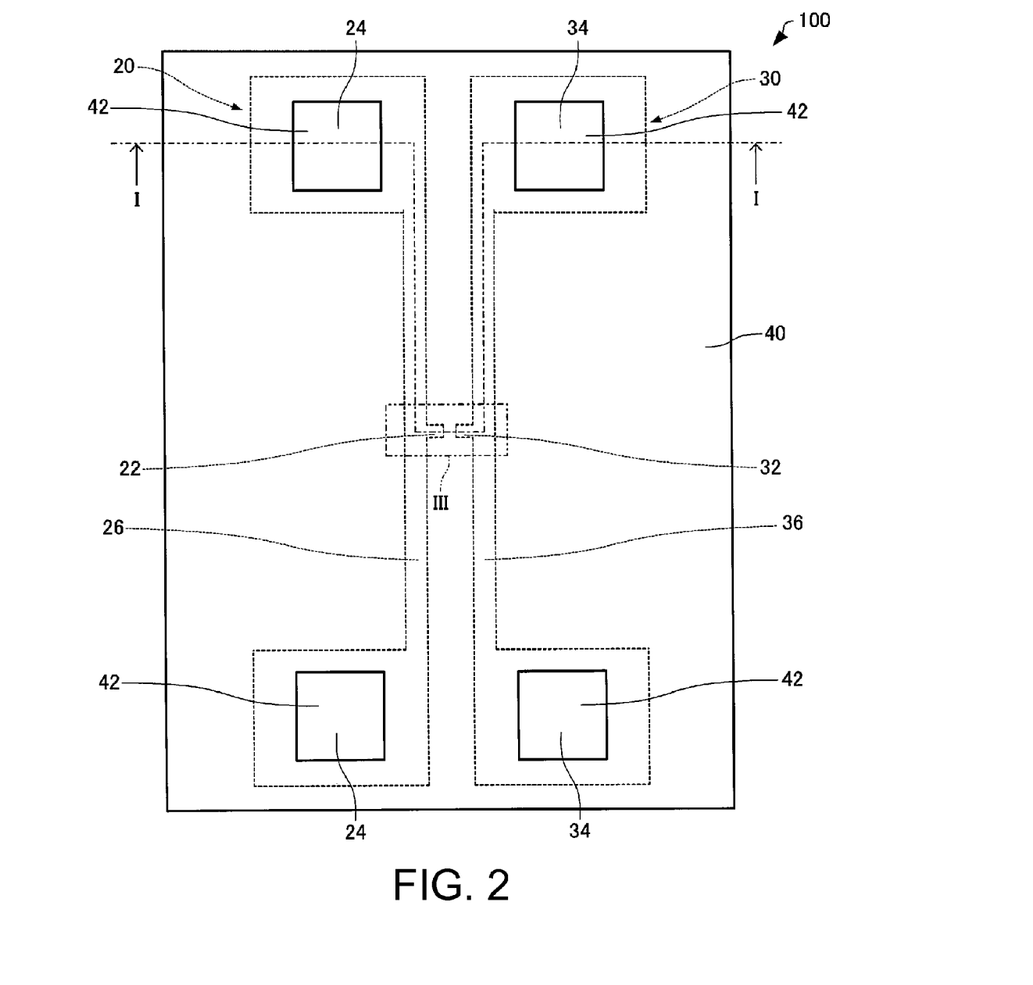
FIG. 2 is a plan view schematically illustrating the photoconductive antenna according to the present embodiment.
Figure 3:
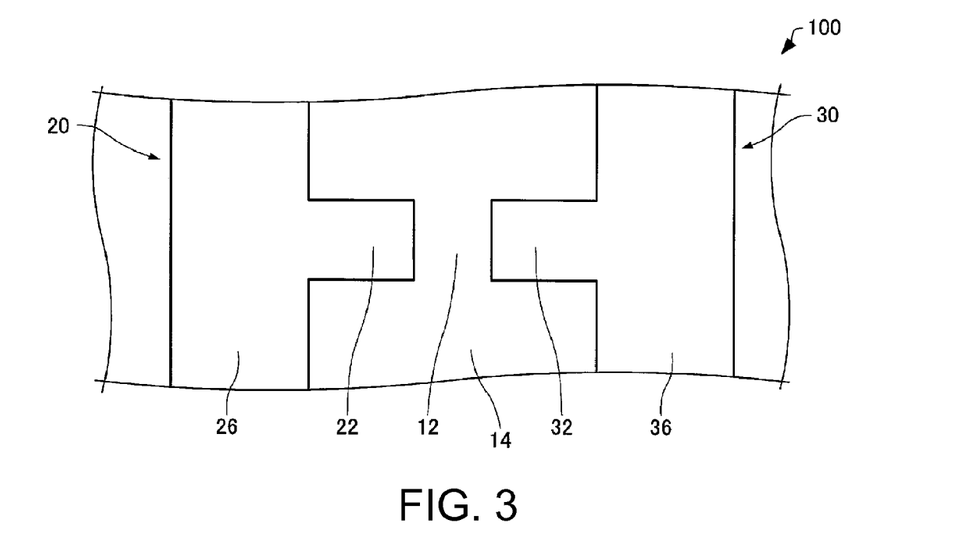
FIG. 3 is a plan view schematically illustrating the photoconductive antenna according to the present embodiment.

First, a photoconductive antenna according to the present embodiment will be described with reference to the accompanying drawings. FIG. 1 is a cross-sectional view schematically illustrating a photoconductive antenna 100 according to the present embodiment. FIGS. 2 and 3 are plan views schematically illustrating the photoconductive antenna 100 according to the present embodiment. Meanwhile, FIG. 1 is a cross-sectional view taken along line I-I of FIG. 2. In addition, FIG. 3 is an enlarged view of a region III shown in FIG. 2. In addition, for convenience, an insulating layer 40 is not shown in FIG. 3.

As shown in FIGS. 1 to 3, the photoconductive antenna 100 includes a carrier generation layer 10, a first electrode 20, a second electrode 30, and the insulating layer 40. The photoconductive antenna 100 generates a terahertz wave T by irradiation with a light pulse P.

Meanwhile, the term "light pulse" as used herein refers to light of which the intensity changes drastically in a short period of time. The pulse width (full width at half maximum: FWHM) of the light pulse is not particularly limited, but is, for example, equal to or greater than 1 fs (femtosecond) and equal to or less than 800 fs. In addition, the "terahertz wave" refers to an electromagnetic wave having a frequency of equal to or greater than 100 GHz and equal to or less than 30 THz, particularly, an electromagnetic wave having a frequency of equal to or greater than 300 GHz and equal to or less than 3 THz.

The carrier generation layer 10 is constituted by, for example, a semi-insulating substrate. The term "semi-insulating substrate" as used herein refers to a substrate which is constituted by a compound-semiconductor, and a high-resistance (for example, specific resistance is equal to or greater than $10^7$ Ω·cm) substrate. Specifically, the semi-insulating substrate constituting the carrier generation layer 10 is a GaAs substrate which does not contain impurities (which is not doped with impurities). GaAs constituting the carrier generation layer 10 may be in a stoichiometric state. That is, Ga and As constituting the carrier generation layer 10 may be present at a proportion of 1:1. Meanwhile, the semi-insulating substrate constituting the carrier generation layer 10 may be an InP substrate, an InAs substrate, or an InSb substrate.

The carrier generation layer 10 forms carriers C by irradiation with the light pulse P. Specifically, the carrier generation layer 10 forms a plurality of (a large number of)

carriers C. When the carrier generation layer 10 is formed of a semi-insulating GaAs substrate, the carrier mobility (electron mobility) of the carrier generation layer 10 is, for example, equal to or greater than 3,000 cm$^2$/Vs and equal to or less than 8,500 cm$^2$/Vs.

Meanwhile, the term "carrier mobility" as used herein refers to a distance which carriers (electrons and holes) transfer per unit hour under a unit electric field intensity when the carriers transfer through a solid-state substance, and a tendency for the carriers to transfer through a solid-state substance.

The first electrode 20 and the second electrode 30 are located on the carrier generation layer 10. The first electrode 20 and the second electrode 30 are electrodes that apply a voltage to the carrier generation layer 10. The electrodes 20 and 30 may apply a direct-current (DC) voltage to the carrier generation layer 10, and may apply an alternating-current (AC) voltage thereto. The electrodes 20 and 30 may be brought into ohmic contact with the carrier generation layer 10.

The first electrode 20 and the second electrode 30 are, for example, an Au layer, a Pt layer, a Ti layer, an Al layer, a Cu layer, a Cr layer, or a laminated body thereof. When the laminated body of an Au layer and a Cr layer is used as the electrodes 20 and 30, the Cr layer can improve adhesion between the carrier generation layer 10 and the Au layer.

The first electrode 20 includes a first voltage application portion 22, a first pad portion 24, and a first line portion 26. The second electrode 30 includes a second voltage application portion 32, a second pad portion 34, and a second line portion 36.

The first voltage application portion 22 and the second voltage application portion 32 are portions that apply a voltage to the carrier generation layer 10. A distance between the first voltage application portion 22 and the second voltage application portion 32 is, for example, equal to or greater than 1 μm and equal to or less than 100 μm, and more specifically, is approximately 5 μm. In the shown example, the planar shape of the voltage application portions 22 and 32 (shape when seen from the lamination direction of the carrier generation layer 10 and the insulating layer 40) is rectangular. That is, the photoconductive antenna 100 is a dipole PCA.

Meanwhile, although not shown in the drawing, the first voltage application portion 22 may have a trapezoidal planar shape having a narrower width toward the second voltage application portion 32 side. Similarly, the second voltage application portion 32 may have a trapezoidal planar shape having a narrower width toward the first voltage application portion 22 side. That is, the photoconductive antenna 100 may be a bow-tie PCA.

The first pad portion 24 and the second pad portion 34 are portions which are connected to an external wiring (not shown). In the shown example, the planar shape of the pad portions 24 and 34 is rectangular. The number of first pad portions 24 provided is, for example, two. The number of second pad portions 34 provided is, for example, two.

The first line portion 26 connects the first voltage application portion 22 and the first pad portion 24. The second line portion 36 connects the second voltage application portion 32 and the second pad portion 34. The line portions 26 and 36 have a belt-like shape when seen in a plan view, and the longitudinal direction of the line portions 26 and 36 is, for example, parallel. The first voltage application portion 22 protrudes from the first line portion 26 in a direction perpendicular to the longitudinal direction of the first line portion 26. The first voltage application portion 22 protrudes from the first line portion 26 to the second electrode 30 side. The second voltage application portion 32 protrudes from the second line portion 36 in a direction perpendicular to the longitudinal direction of the second line portion 36. The second voltage application portion 32 protrudes from the second line portion 36 to the first electrode 20 side.

The insulating layer 40 is located on the carrier generation layer 10. Specifically, the insulating layer 40 is provided on a region 12 which is irradiated with the light pulse P between the first electrode 20 and the second electrode 30, when seen in a plan view (when seen from the lamination direction of the carrier generation layer 10 and the insulating layer 40). The region 12 is a portion of a surface 14 of the carrier generation layer 10. The surface 14 is the upper surface of the carrier generation layer 10. In the shown example, the insulating layer 40 is provided on the carrier generation layer 10 and on the electrodes 20 and 30. The insulating layer 40 is provided with an opening 42. The opening 42 is provided at a position overlapping the pad portions 24 and 34 when seen in a plan view, and the pad portions 24 and 34 are exposed from the insulating layer 40.

The thickness of the insulating layer 40 is, for example, equal to or greater than 100 nm and equal to or less than 500 nm. The insulating layer 40 is capable of transmitting the light pulse P. Specifically, the wavelength of the light pulse P is equal to or greater than 700 nm and equal to or less than 800 nm, and the insulating layer 40 is capable of transmitting 80% or more of the light pulse P having such a wavelength. The insulating layer 40 is formed of, for example, any of silicon oxide (SiO$_2$), silicon nitride (SiN), a compound of aluminum gallium arsenide (AlGaAs) and oxygen, and polyimide. The compound of aluminum gallium arsenide and oxygen is, for example, a compound obtained by oxidizing aluminum gallium arsenide.

The insulating layer 40 terminates a dangling bond located on the surface 14 of the carrier generation layer 10. Here, the wording "dangling bond located on the surface of the carrier generation layer" refers to a bonding hand occupied with electrons (unpaired electrons) which are not involved in bonding (for example, bonding between gallium and arsenic) between atoms constituting the surface 14 of the carrier generation layer 10. Further, the wording "terminating a dangling bond" refers to bonding to a dangling bond located on the surface 14 of the carrier generation layer 10. That is, the atoms constituting the insulating layer 40 can be bonded to a bonding hand occupied with electrons which are not involved in bonding between atoms constituting the surface 14 of the carrier generation layer 10. Specifically, the atoms (for example, silicon or oxygen) constituting the insulating layer 40 can be covalently bonded to atoms (for example, gallium or arsenic) having unpaired electrons of the carrier generation layer 10.

Next, operations of the photoconductive antenna 100 will be described. In a state where a voltage is applied to the carrier generation layer 10 by the electrodes 20 and 30, irradiation with the light pulse P between the electrodes 20 and 30 (between the voltage application portions 22 and 32) is performed. The light pulse P passes through the insulating layer 40 and the region 12 of the carrier generation layer 10 is irradiated with the light pulse P.

The carriers (for example, electrons) C are instantaneously generated in the carrier generation layer 10 by irradiation with the light pulse P. The carriers C are accelerated by the voltage applied by the electrodes 20 and 30 and transfer (travel) through the carrier generation layer 10, and thus a current (photocurrent) flows instantaneously in the carrier generation layer 10. The terahertz wave T having an intensity proportional to the time variation of the photocurrent is generated. The time variation of the photocurrent is proportional to the carrier mobility of the carrier generation layer 10. Therefore, the terahertz wave T having an intensity proportional to the carrier mobility of the carrier generation layer 10 is generated in the photoconductive antenna 100.

Meanwhile, in the shown example, the carriers C transfer from the first electrode 20 side toward the second electrode 30 side, but may transfer from the second electrode 30 side toward the first electrode 20 side. In addition, insofar as the region 12 is irradiated with the light pulse P, a position or an area which is irradiated with the light pulse P is not particularly limited.

The photoconductive antenna 100 has, for example, the following features.

The photoconductive antenna 100 has the carriers C formed therein by irradiation with the light pulse P, and includes the carrier generation layer 10 constituted by a semi-insulating substrate. The carriers C which are generated in the carrier generation layer 10 can travel through the carrier generation layer 10. The semi-insulating substrate can have higher carrier mobility (electron mobility) than that of an LT-GaAs layer. Therefore, in the photoconductive antenna 100, it is possible to further enhance carrier mobility than in a case where the carrier generation layer is formed of an LT-GaAs layer, and to generate (radiate) a terahertz wave having a large intensity. Therefore, in the photoconductive antenna 100, it is possible to achieve an increase in power.

Further, in the photoconductive antenna 100, the insulating layer 40 is provided on the region 12 which is irradiated with the light pulse P between the first electrode 20 and the second electrode 30, when seen in a plan view. Here, since the atoms constituting the surface 14 of the carrier generation layer 10 have a dangling bond, the carriers C traveling along the vicinity of the surface 14 of the carrier generation layer 10 may be trapped by the dangling bond. For this reason, when an insulating layer is not provided on the surface (region 12) of the carrier generation layer, impurities are attached to the surface of the carrier generation layer, for example, during the use of the photoconductive antenna and thus the carrier generation layer reacts with the impurities. Thereby, the degree of the carriers being trapped by the dangling bond may change. That is, the state of the surface 14 of the carrier generation layer 10 changes over time due to the reaction of the carrier generation layer with the impurities, and thus the degree of the carriers being trapped by the dangling bond may change. For this reason, the photoconductive antenna may be required to be calibrated. Since the atoms constituting the surface 14 of the carrier generation layer 10 have the dangling bond, the atoms have high reactivity, and have a tendency to react with the attached impurities.

Regarding the above-mentioned problem, in the photoconductive antenna 100, impurities can be prevented from being attached to the region 12 of the carrier generation layer 10 by the insulating layer 40. As a result, the photoconductive antenna 100 can prevent the degree of the carriers being trapped from changing due to the impurities, and have high reliability.

In the photoconductive antenna 100, the insulating layer 40 terminates the dangling bond located on the surface 14 of the carrier generation layer 10. Therefore, in the photoconductive antenna 100, it is possible to prevent the carriers C traveling along the vicinity of the surface 14 of the carrier generation layer 10 from being trapped by the dangling bond. Therefore, in the photoconductive antenna 100, it is possible to achieve an increase in power.

In the photoconductive antenna 100, the insulating layer 40 is formed of any of silicon oxide, silicon nitride, or a compound of aluminum gallium arsenide and oxygen. Therefore, the atoms constituting the insulating layer 40 can be bonded to the atoms constituting the surface 14 of the carrier generation layer 10 by a dangling bond which is not involved in bonding in the carrier generation layer 10. Thereby, in the photoconductive antenna 100, it is possible to prevent the carriers C traveling along the vicinity of the surface 14 of the carrier generation layer 10 from being trapped by the dangling bond. Therefore, in the photoconductive antenna 100, it is possible to achieve an increase in power.

2. Method of Manufacturing Photoconductive Antenna

Figure 4:
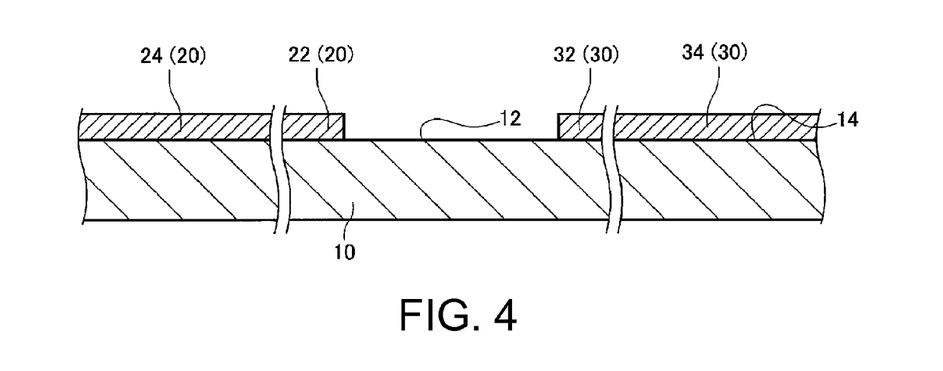
FIG. 4 is a cross-sectional view schematically illustrating a process of manufacturing the photoconductive antenna according to the present embodiment.

Next, a method of manufacturing the photoconductive antenna 100 according to the present embodiment will be described with reference to the accompanying drawings. FIG. 4 is a cross-sectional view schematically illustrating a process of manufacturing the photoconductive antenna 100 according to the present embodiment, and corresponds to FIG. 1.

As shown in FIG. 4, the first electrode 20 and the second electrode 30 are formed on the carrier generation layer 10. The electrodes 20 and 30 are formed by, for example, a combination of a vacuum vapor deposition method and a lift-off method, or the like.

As shown in FIG. 1, the insulating layer 40 is formed on the carrier generation layer 10 and on the electrodes 20 and 30. Specifically, an insulating layer (not shown) is formed on the carrier generation layer 10 and on the electrodes 20 and 30, using, for example, a CVD (Chemical Vapor Deposition) method, a sputtering method, an EB evaporation method, or the like, and the insulating layer 40 is formed by patterning the insulating layer. The patterning is performed by, for example, photolithography and etching.

The photoconductive antenna 100 can be manufactured by the above processes.

Figure 5:
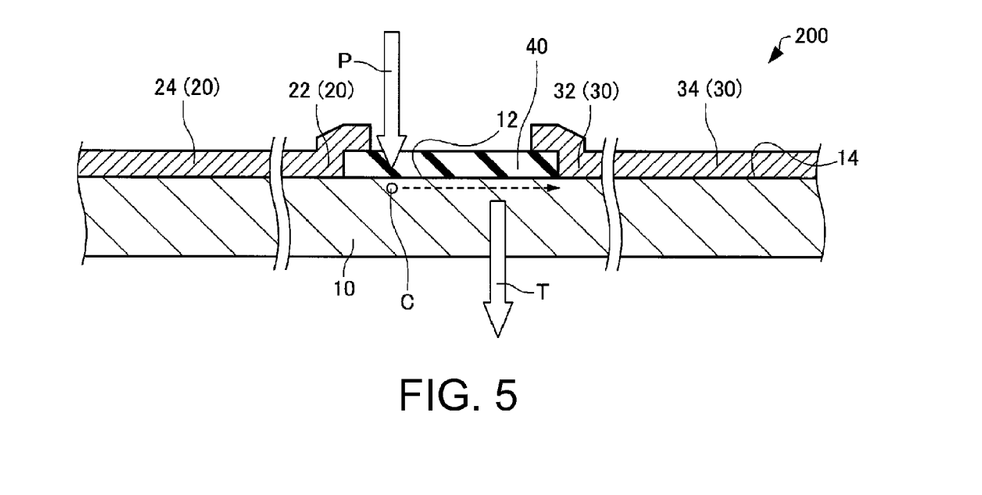
FIG. 5 is a cross-sectional view schematically illustrating a photoconductive antenna according to a first modification example of the present embodiment.

3. Modification Example of Photoconductive Antenna 3.1. First Modification Example Next, a photoconductive antenna according to a first modification example of the present embodiment will be described with reference to the accompanying drawings. FIG. 5 is a cross-sectional view schematically illustrating a photoconductive antenna 200 according to the first modification example of the present embodiment, and corresponds to FIG. 1.

Hereinafter, in the photoconductive antenna 200 according to the first modification example of the present embodiment, members having the same functions as those of the configuration members of the photoconductive antenna 100 according to the present embodiment are assigned the same reference numerals and signs, and thus the detailed description thereof will be omitted. The same is true of a photoconductive antenna according to a second modification example of the present embodiment described below.

As shown in FIG. 1, in the aforementioned photoconductive antenna 100, the first electrode 20 and the second electrode 30 are provided on the carrier generation layer 10.

On the other hand, in the photoconductive antenna 200, as shown in FIG. 5, a portion of the first electrode 20 and a portion of the second electrode 30 are provided on the insulating layer 40. Specifically, a portion of the first voltage application portion 22 and a portion of the second voltage application portion 32 are provided on the insulating layer 40. The insulating layer 40 may be provided on only the region 12, and may also be provided on the surface 14 other than the region 12.

The photoconductive antenna 200 is manufactured by first forming the insulating layer 40 on the carrier generation layer 10, and next forming the electrodes 20 and 30 on the carrier generation layer 10 and on the insulating layer 40.

3.2. Second Modification Example

Figure 6:
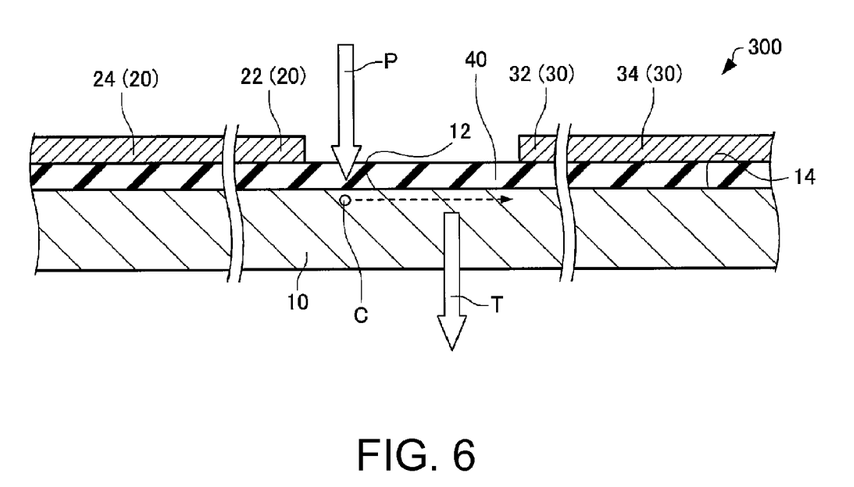
FIG. 6 is a cross-sectional view schematically illustrating a photoconductive antenna according to second modification example of the present embodiment.

Next, a photoconductive antenna according to a second modification example of the present embodiment will be described with reference to the accompanying drawings. FIG. 6 is a cross-sectional view schematically illustrating a photoconductive antenna 300 according to the second modification example of the present embodiment, and corresponds to FIG. 1.

In the aforementioned photoconductive antenna 100, as shown in FIG. 1, the first electrode 20 and the second electrode 30 are provided on the carrier generation layer 10. On the other hand, in the photoconductive antenna 300, as shown in FIG. 6, the first electrode 20 and the second electrode 30 are provided on the insulating layer 40. In the shown example, the entire first electrode 20 and the entire second electrode 30 are provided on the insulating layer 40.

In the photoconductive antenna 300, the insulating layer 40 is provided on, for example, the entire surface 14 of the carrier generation layer 10. The thickness of the insulating layer 40 is of such an extent that a voltage is applied to the carrier generation layer 10 by the electrodes 20 and 30.

The photoconductive antenna 300 is manufactured by first forming the insulating layer 40 on the carrier generation layer 10, and next forming the electrodes 20 and 30 on the insulating layer 40.

In the photoconductive antenna 300, the first electrode 20 and the second electrode 30 are provided on the insulating layer 40. Therefore, in the photoconductive antenna 300, it is possible to suppress a flow of a leakage current between the electrodes 20 and 30, and to improve a breakdown voltage. As a result, the photoconductive antenna 300 has high reliability, and can improve a yield rate. Further, it is possible to reduce power consumption.

4. Terahertz Wave Generation Device

Figure 7:
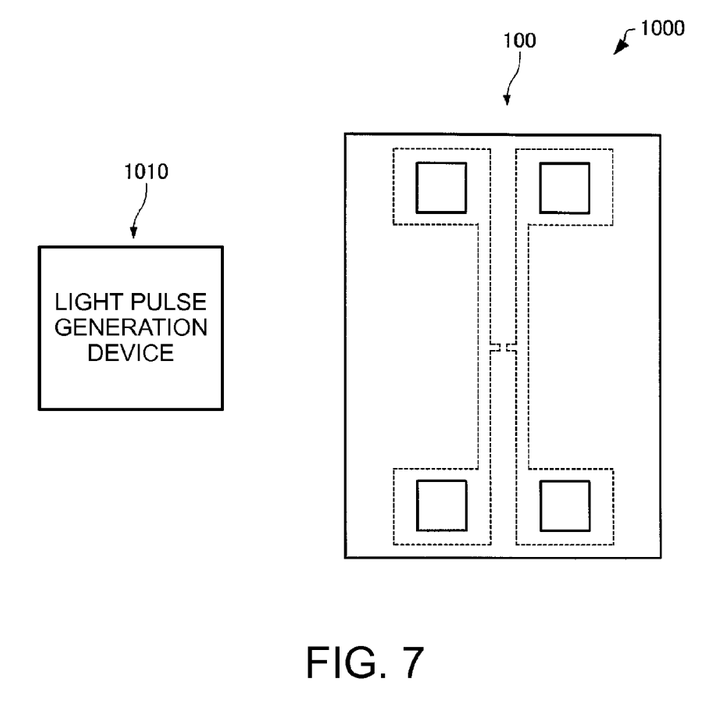
FIG. 7 is a diagram illustrating a configuration of a terahertz wave generation device according to the present embodiment.

Next, a terahertz wave generation device 1000 according to the present embodiment will be described with reference to the accompanying drawings. FIG. 7 is a diagram illustrating a configuration of the terahertz wave generation device 1000 according to the present embodiment.

As shown in FIG. 7, the terahertz wave generation device 1000 includes a light pulse generation device 1010 and the photoconductive antenna according to the invention. Hereinafter, an example will be described in which the photoconductive antenna 100 is used as the photoconductive antenna according to the invention.

The light pulse generation device 1010 generates a light pulse (for example, light pulse P shown in FIG. 1) which is excitation light. The light pulse generation device 1010 irradiates the photoconductive antenna 100. The width of the light pulse which is generated by the light pulse generation device 1010 is, for example, equal to or greater than 1 fs and equal to or less than 800 fs. As the light pulse generation device 1010, for example, a femtosecond fiber laser or a titanium sapphire laser is used.

As described above, the photoconductive antenna 100 can generate a terahertz wave by irradiation with a light pulse.

The terahertz wave generation device 1000 includes the photoconductive antenna 100, and thus can improve an increase in power.

5. Imaging Device

Figure 8:
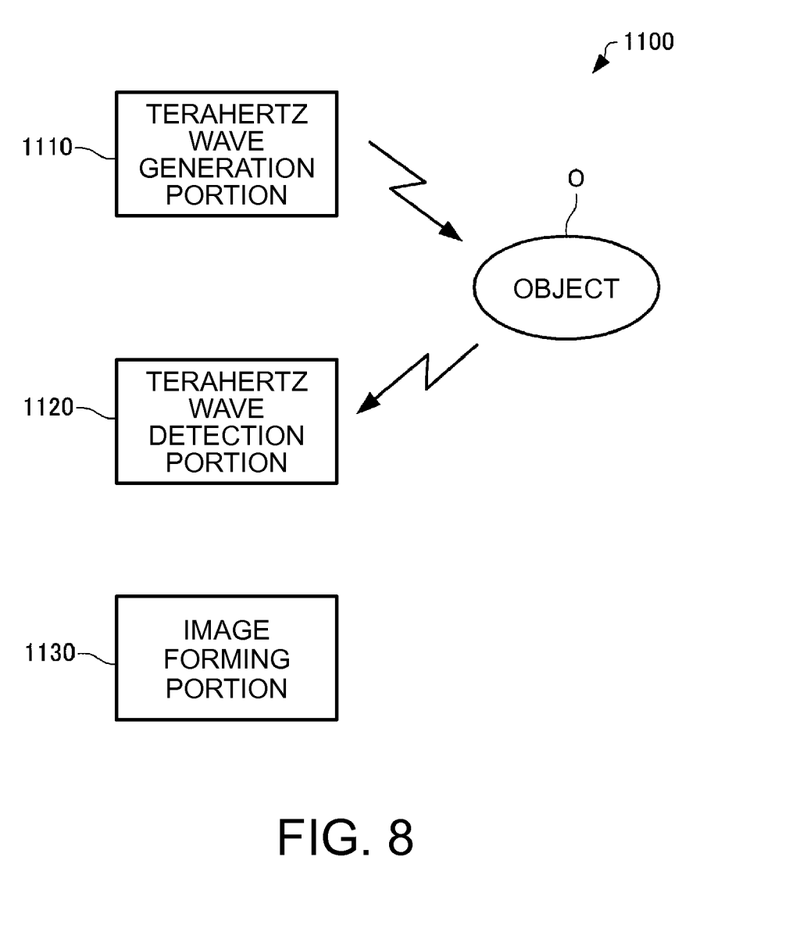
FIG. 8 is a block diagram illustrating an imaging device according to the present embodiment.
Figure 9:
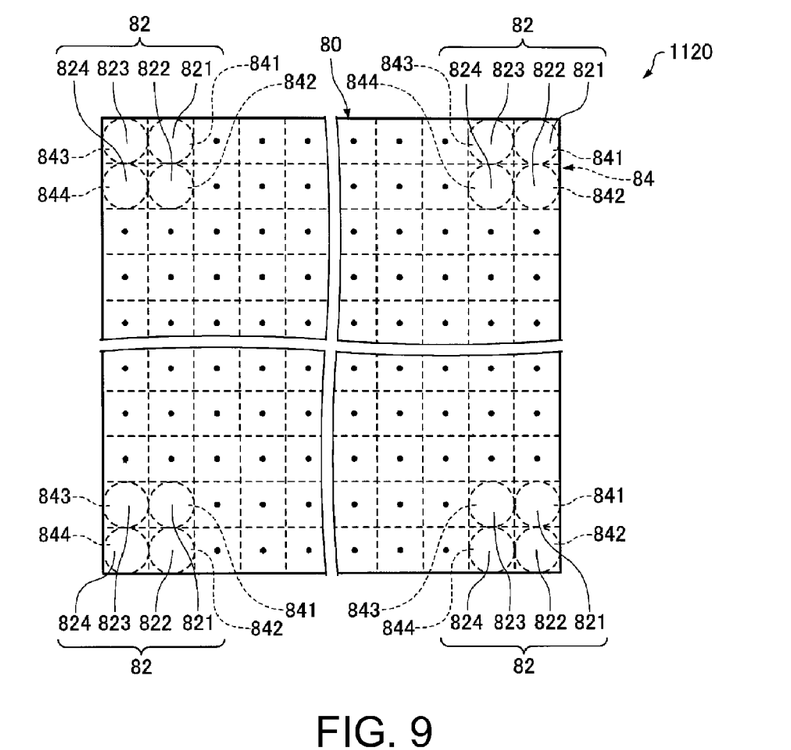
FIG. 9 is a plan view schematically illustrating a terahertz wave detection portion of the imaging device according to the present embodiment.
Figure 10:
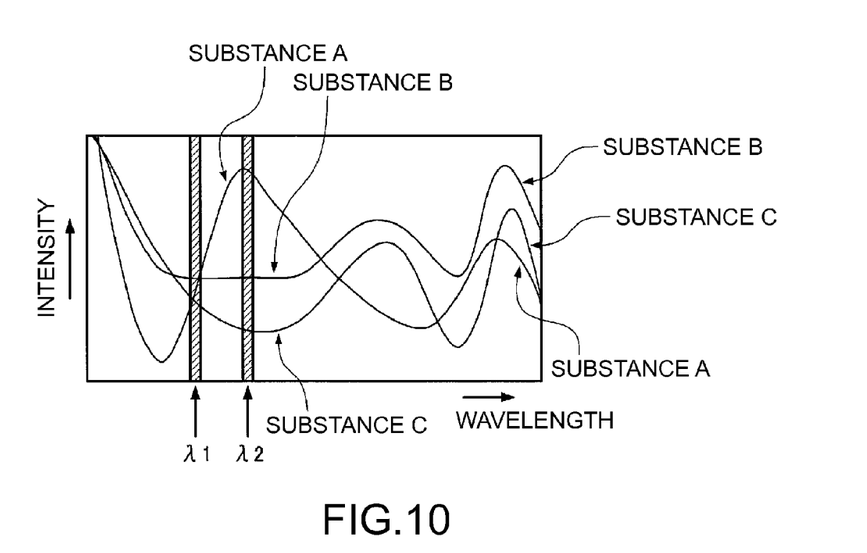
FIG. 10 is a graph illustrating a spectrum of an object in a terahertz band.
Figure 11:
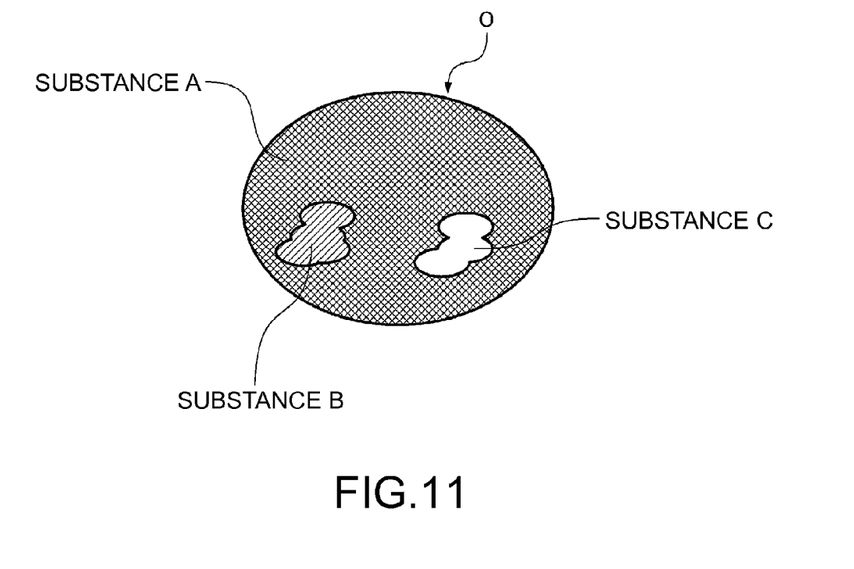
FIG. 11 is an image diagram illustrating a distribution of substances of the object.

Next, an imaging device 1100 according to the present embodiment will be described with reference to the accompanying drawings. FIG. 8 is a block diagram illustrating the imaging device 1100 according to the present embodiment. FIG. 9 is a plan view schematically illustrating a terahertz wave detection portion 1120 of the imaging device 1100 according to the present embodiment. FIG. 10 is a graph illustrating a spectrum of an object in a terahertz band. FIG. 11 is an image diagram illustrating a distribution of substances A, B and C of the object.

As shown in FIG. 8, the imaging device 1100 includes a terahertz wave generation portion 1110 that generates a terahertz wave, a terahertz wave detection portion 1120 that detects a terahertz wave emitted from the terahertz wave generation portion 1110 and passing through an object O or a terahertz wave reflected from the object O, and an image forming portion 1130 that generates an image of the object O, that is, image data on the basis of a detection result of the terahertz wave detection portion 1120.

As the terahertz wave generation portion 1110, a terahertz wave generation device according to the invention can be used. Here, a case will be described in which the terahertz wave generation device 1000 is used as the terahertz wave generation device according to the invention.

The terahertz wave detection portion 1120 to be used includes a filter 80 that transmits a terahertz wave having an objective wavelength and a detection portion 84 that detects the terahertz wave having an objective wavelength having passed through the filter 80, as shown in FIG. 9. In addition, the detection portion 84 to be used has, for example, a function of converting a terahertz wave into heat to detect the converted terahertz wave, that is, a function capable of converting a terahertz wave into heat to detect energy (intensity) of the terahertz wave. Such a detection portion includes, for example, a pyroelectric sensor, a bolometer or the like. Meanwhile, the configuration of the terahertz wave detection portion 1120 is not limited to the above-mentioned configuration.

In addition, the filter 80 includes a plurality of pixels (unit filter portions) 82 which are arranged two-dimensionally. That is, the respective pixels 82 are arranged in a matrix.

In addition, each of the pixels 82 includes a plurality of regions that transmit terahertz waves having wavelengths different from each other, that is, a plurality of regions in which wavelengths of terahertz waves to be transmitted (hereinafter, referred to as "transmission wavelengths") are different from each other. Meanwhile, in the shown configuration, each of the pixels 82 includes a first region 821, a second region 822, a third region 823, and a fourth region 824.

In addition, the detection portion 84 includes a first unit detection portion 841, a second unit detection portion 842, a third unit detection portion 843 and a fourth unit detection portion 844 which are respectively provided corresponding to the first region 821, the second region 822, the third region 823 and the fourth region 824 of each pixel 82 of the filter 80. Each first unit detection portion 841, each second unit detection portion 842, each third unit detection portion 843 and each fourth unit detection portion 844 convert terahertz waves which have respectively passed through the first region 821, the second region 822, the third region 823 and the fourth region 824 of each pixel 82 into heat to detect the converted terahertz waves. Thereby, it is possible to reliably detect the terahertz waves having four objective wavelengths in the respective regions of each pixel 82.

Next, an example of use of the imaging device 1100 will be described.

First, the object O targeted for spectroscopic imaging is constituted by three substances A, B and C. The imaging device 1100 performs spectroscopic imaging on the object O. In addition, here, as an example, the terahertz wave detection portion 1120 is assumed to detect a terahertz wave reflected from the object O.

In addition, the first region 821 and the second region 822 are used in each pixel 82 of the filter 80 of the terahertz wave detection portion 1120. When the transmission wavelength of the first region 821 is set to $\lambda 1$, the transmission wavelength of the second region 822 is set to $\lambda 2$, the intensity of a component having the wavelength $\lambda 1$ of the terahertz wave reflected from the object O is set to $\alpha 1$, and the intensity of a component having the wavelength $\lambda 2$ is set to $\alpha 2$, the transmission wavelength $\lambda 1$ of the first region 821 and the transmission wavelength $\lambda 2$ of the second region 822 are set so that differences ($\alpha 2 - \alpha 1$) between the intensity $\alpha 2$ and the intensity $\alpha 1$ can remarkably distinguish from each other in the substance A, the substance B and the substance C.

As shown in FIG. 10, in the substance A, the difference ($\alpha 2 - \alpha 1$) between the intensity $\alpha 2$ of the component having the wavelength $\lambda 2$ of the terahertz wave reflected from the object O and the intensity $\alpha 1$ of the component having the wavelength $\lambda 1$ is set to a positive value. In addition, in the substance B, the difference ($\alpha 2 - \alpha 1$) between the intensity $\alpha 2$ and the intensity $\alpha 1$ is set to zero. In addition, in the substance C, the difference ($\alpha 2 - \alpha 1$) between the intensity $\alpha 2$ and the intensity $\alpha 1$ is set to a negative value.

When the spectroscopic imaging of the object O is performed by the imaging device 1100, a terahertz wave is first generated by the terahertz wave generation portion 1110, and the object O is irradiated with the terahertz wave. The terahertz wave reflected from the object O is then detected as $\alpha 1$ and $\alpha 2$ in the terahertz wave detection portion 1120. The detection results are sent out to the image forming portion 1130. Meanwhile, the irradiation of the object O with the terahertz wave and the detection of the terahertz wave reflected from the object O are performed on the entire object O.

In the image forming portion 1130, the difference ($\alpha 2 - \alpha 1$) between the intensity $\alpha 2$ of the component having the wavelength $\lambda 2$ of the terahertz wave having passed through the second region 822 of the filter 80 and the intensity $\alpha 1$ of the component having the wavelength $\lambda 1$ of the terahertz wave having passed through the first region 821 is obtained on the basis of the above detection results. In the object O, a region in which the difference is set to a positive value is determined to be the substance A, a region in which the difference is set to zero is determined to be the substance B, and a region in which the difference is set to a negative value is determined to be the substance C, and the respective regions are specified.

In addition, in the image forming portion 1130, image data of an image indicating the distribution of the substances A, B and C of the object O is created as shown in FIG. 11.

The image data is sent out from the image forming portion 1130 to a monitor which is not shown, and the image indicating the distribution of the substances A, B and C of the object O is displayed on the monitor. In this case, for example, using color coding, the region in which the substance A of the object O is distributed is displayed in a black color, the region in which the substance B is distributed is displayed in an ash color, and the region in which the substance C is distributed is displayed in a white color. In the imaging device 1100, in this manner, the identification of each substance constituting the object O and the distribution measurement of each substance can be simultaneously performed.

Meanwhile, the application of the imaging device 1100 is not limited to the above. For example, a person is irradiated with a terahertz wave, the terahertz wave transmitted or reflected through or from the person is detected, and a process is performed in the image forming portion 1130, and thus it is possible to discriminate whether the person carries a pistol, a knife, an illegal medicinal substance, and the like.

The imaging device 1100 includes the photoconductive antenna 100 which is capable of achieving an increase in power. For this reason, the imaging device 1100 can have high detection sensitivity.

6. Measurement Device

Figure 12:
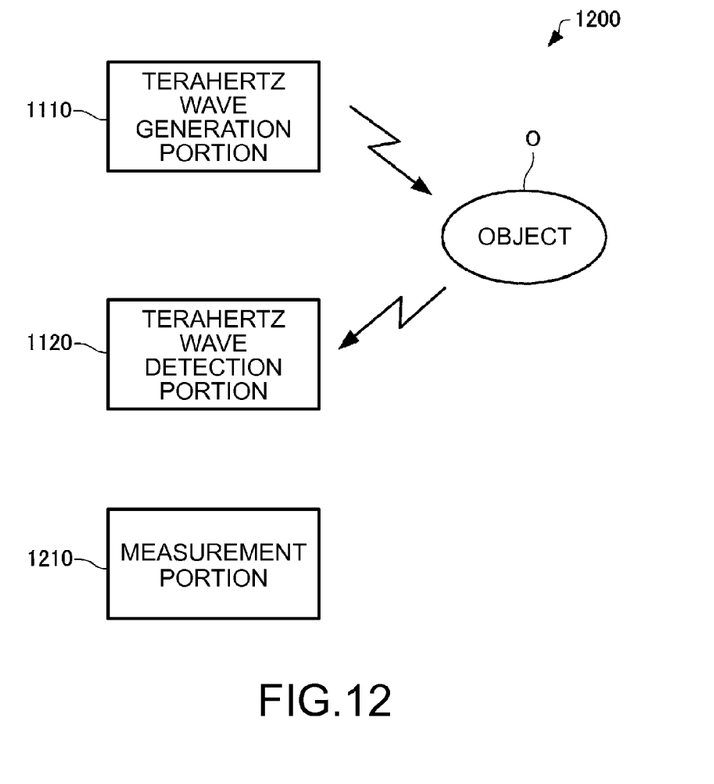
FIG. 12 is a block diagram illustrating a measurement device according to the present embodiment.

Next, a measurement device 1200 according to the present embodiment will be described with reference to the accompanying drawings. FIG. 12 is a block diagram illustrating the measurement device 1200 according to the present embodiment. In the measurement device 1200 according to the present embodiment described below, members having the same functions as those of the configuration members of the aforementioned imaging device 1100 are assigned the same reference numerals and signs, and thus the detailed description thereof will be omitted.

As shown in FIG. 12, the measurement device 1200 includes a terahertz wave generation portion 1110 that generates a terahertz wave, a terahertz wave detection portion 1120 that detects a terahertz wave emitted from the terahertz wave generation portion 1110 and passing through the object O or a terahertz wave reflected from the object O, and a measurement portion 1210 that measures the object O on the basis of a detection result of the terahertz wave detection portion 1120.

Next, an example of use of the measurement device 1200 will be described. When the spectroscopic measurement of the object O is performed by the measurement device 1200, a terahertz wave is first generated by the terahertz wave generation portion 1110, and the object O is irradiated with the terahertz wave. The terahertz wave having passed through the object O or a terahertz wave reflected from the object O is then detected in the terahertz wave detection portion 1120. The detection results are sent out to the measurement portion 1210. Meanwhile, the irradiation of the object O with the terahertz wave and the detection of the terahertz wave having passed through the object O or the terahertz wave reflected from the object O are performed on the entire object O.

In the measurement portion 1210, the intensity of each terahertz wave having passed through the first region 821, the second region 822, the third region 823 and the fourth region 824 of each pixel 82 of the filter 80 is ascertained from the above detection results, and the analysis or the like of components of the object O and the distribution thereof is performed.

The measurement device 1200 includes the photoconductive antenna 100 which is capable of achieving an increase in power. For this reason, the measurement device 1200 can have high detection sensitivity.

7. Camera

Figure 13:
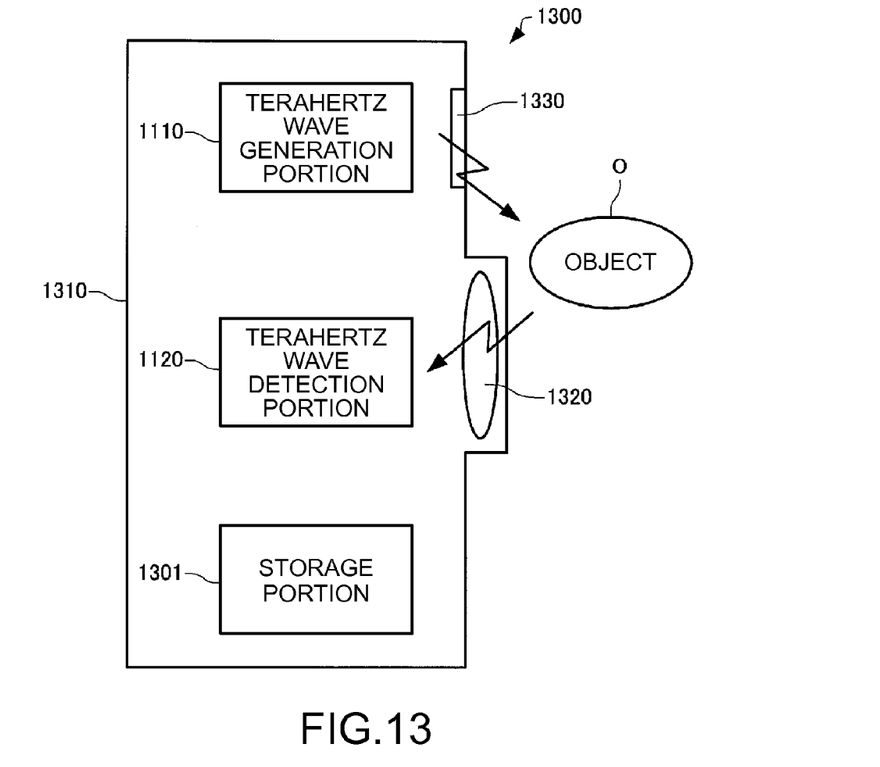
FIG. 13 is a block diagram illustrating a camera according to the present embodiment.
Figure 14:
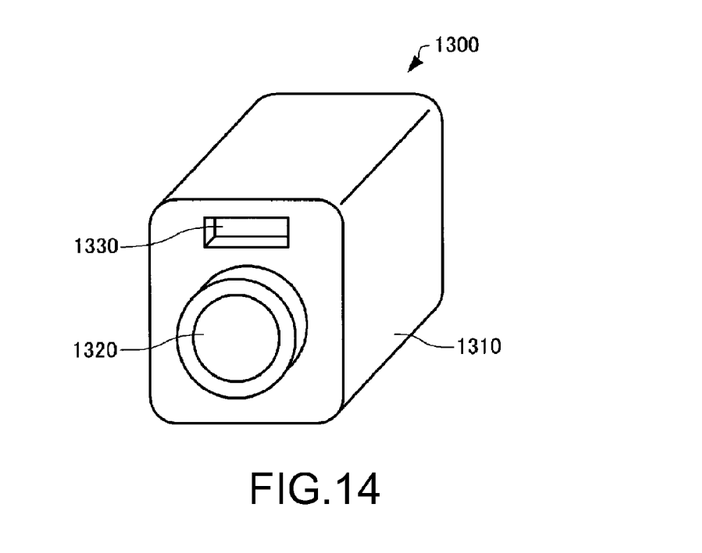
FIG. 14 is a perspective view schematically illustrating the camera according to the present embodiment.

Next, a camera 1300 according to the present embodiment will be described with reference to the accompanying drawings. FIG. 13 is a block diagram illustrating the camera 1300 according to the present embodiment. FIG. 14 is a perspective view schematically illustrating the camera 1300 according to the present embodiment. In the camera 1300 according to the present embodiment described below, members having the same functions as those of the configuration members of the aforementioned imaging device 1100 are assigned the same reference numerals and signs, and thus the detailed description thereof will be omitted.

As shown in FIGS. 13 and 14, the camera 1300 includes a terahertz wave generation portion 1110 that generates a terahertz wave, a terahertz wave detection portion 1120 that detects a terahertz wave emitted from the terahertz wave generation portion 1110 and passing through the object O or a terahertz wave reflected from the object O, and a storage portion 1301. The respective portions 1110, 1120, and 1301 are contained in a housing 1310 of the camera 1300. In addition, the camera 1300 includes a lens (optical system) 1320 that converges (images) the terahertz wave reflected from the object O onto the terahertz wave detection portion 1120, and a window 1330 that emits the terahertz wave generated in the terahertz wave generation portion 1110 to the outside of the housing 1310. The lens 1320 and the window 1330 are constituted by members, such as silicon, quartz, or polyethylene, which transmit and refract the terahertz wave. Meanwhile, the window 1330 may have a configuration in which an opening is simply provided as in a slit.

Next, an example of use of the camera 1300 will be described. When the object O is imaged by the camera 1300, a terahertz wave is first generated by the terahertz wave generation portion 1110, and the object O is irradiated with the terahertz wave. The terahertz wave reflected from the object O is converged (imaged) onto the terahertz wave detection portion 1120 by the lens 1320 to detect the converged wave. The detection results are sent out to the storage portion 1301 and are stored therein. Meanwhile, the irradiation of the object O with the terahertz wave and the detection of the terahertz wave reflected from the object O are performed on the entire object O. In addition, the above detection results can also be transmitted to, for example, an external device such as a personal computer. In the personal computer, each process can be performed on the basis of the above detection results.

The camera 1300 includes the photoconductive antenna 100 which is capable of achieving an increase in power. For this reason, the camera 1300 can have high detection sensitivity.

The above-mentioned embodiments and modification examples are illustrative examples, and are not limited thereto. For example, each of the embodiments and each of the modification examples can also be appropriately combined.

The invention includes substantially the same configurations (for example, configurations having the same functions, methods and results, or configurations having the same objects and effects) as the configurations described in the embodiments. In addition, the invention includes a configuration obtained by replacing non-essential portions in the configurations described in the embodiments. In addition, the invention includes a configuration that exhibits the same operations and effects as those of the configurations described in the embodiment or a configuration capable of achieving the same objects. In addition, the invention includes a configuration obtained by adding the configurations described in the embodiments to known techniques.

The entire disclosure of Japanese Patent Application No. 2014-032798, filed Feb. 24, 2014 is expressly incorporated by reference herein.

What is claimed is:

1. A photoconductive antenna that generates a terahertz wave by irradiation with a light pulse, comprising:
   a carrier generation layer that has carriers formed therein by irradiation with the light pulse, and is constituted by a semi-insulating substrate;
   an insulating layer, located on the carrier generation layer, which is capable of transmitting the light pulse; and
   a first electrode and a second electrode, located above the carrier generation layer, which apply a voltage to the carrier generation layer,
   wherein the insulating layer is provided directly on the carrier generation layer in a region which is irradiated with the light pulse between the first electrode and the second electrode in a plan view, whereas the insulating layer is formed above the first and second electrode layer outside the region which is irradiated with the light pulse.

2. The photoconductive antenna according to claim 1, wherein the first electrode and the second electrode are provided on the insulating layer.

3. A terahertz wave generation device comprising:
   a light pulse generation device that generates a light pulse; and
   the photoconductive antenna according to claim 2 which generates the terahertz wave by irradiation with the light pulse.

4. A camera comprising:
   a light pulse generation device that generates a light pulse;
   the photoconductive antenna according to claim 2 which generates the terahertz wave by irradiation with the light pulse;
   a terahertz wave detection portion that detects the terahertz wave emitted from the photoconductive antenna and passing through an object or the terahertz wave reflected from the object; and
   a storage portion that stores detection results of the terahertz wave detection portion.

5. An imaging device comprising:
   a light pulse generation device that generates a light pulse;
   the photoconductive antenna according to claim 2 which generates the terahertz wave by irradiation with the light pulse;
   a terahertz wave detection portion that detects the terahertz wave emitted from the photoconductive antenna and passing through an object or the terahertz wave reflected from the object; and
   an image forming portion that generates an image of the object on the basis of detection results of the terahertz wave detection portion.

6. A measurement device comprising:
   a light pulse generation device that generates a light pulse;
   the photoconductive antenna according to claim 2 which generates the terahertz wave by irradiation with the light pulse;

a terahertz wave detection portion that detects the terahertz wave emitted from the photoconductive antenna and passing through an object or the terahertz wave reflected from the object; and a measurement portion that measures the object on the basis of detection results of the terahertz wave detection portion.

7. The photoconductive antenna according to claim 1, wherein the insulating layer terminates a dangling bond located on the surface of the carrier generation layer.

8. A terahertz wave generation device comprising:
a light pulse generation device that generates a light pulse; and
the photoconductive antenna according to claim 7 which generates the terahertz wave by irradiation with the light pulse.

9. A camera comprising:
a light pulse generation device that generates a light pulse;
the photoconductive antenna according to claim 7 which generates the terahertz wave by irradiation with the light pulse;
a terahertz wave detection portion that detects the terahertz wave emitted from the photoconductive antenna and passing through an object or the terahertz wave reflected from the object; and
a storage portion that stores detection results of the terahertz wave detection portion.

10. An imaging device comprising:
a light pulse generation device that generates a light pulse;
the photoconductive antenna according to claim 7 which generates the terahertz wave by irradiation with the light pulse;
a terahertz wave detection portion that detects the terahertz wave emitted from the photoconductive antenna and passing through an object or the terahertz wave reflected from the object; and
an image forming portion that generates an image of the object on the basis of detection results of the terahertz wave detection portion.

11. A measurement device comprising:
a light pulse generation device that generates a light pulse;
the photoconductive antenna according to claim 7 which generates the terahertz wave by irradiation with the light pulse;
a terahertz wave detection portion that detects the terahertz wave emitted from the photoconductive antenna and passing through an object or the terahertz wave reflected from the object; and
a measurement portion that measures the object on the basis of detection results of the terahertz wave detection portion.

12. The photoconductive antenna according to claim 1, wherein the insulating layer is formed of any of silicon oxide, silicon nitride, or a compound of aluminum gallium arsenide and oxygen.

13. A terahertz wave generation device comprising:
a light pulse generation device that generates a light pulse; and
the photoconductive antenna according to claim 12 which generates the terahertz wave by irradiation with the light pulse.

14. A camera comprising:
a light pulse generation device that generates a light pulse;
the photoconductive antenna according to claim 12 which generates the terahertz wave by irradiation with the light pulse;
a terahertz wave detection portion that detects the terahertz wave emitted from the photoconductive antenna and passing through an object or the terahertz wave reflected from the object; and
a storage portion that stores detection results of the terahertz wave detection portion.

15. An imaging device comprising:
a light pulse generation device that generates a light pulse;
the photoconductive antenna according to claim 12 which generates the terahertz wave by irradiation with the light pulse;
a terahertz wave detection portion that detects the terahertz wave emitted from the photoconductive antenna and passing through an object or the terahertz wave reflected from the object; and
an image forming portion that generates an image of the object on the basis of detection results of the terahertz wave detection portion.

16. A measurement device comprising:
a light pulse generation device that generates a light pulse;
the photoconductive antenna according to claim 12 which generates the terahertz wave by irradiation with the light pulse;
a terahertz wave detection portion that detects the terahertz wave emitted from the photoconductive antenna and passing through an object or the terahertz wave reflected from the object; and
a measurement portion that measures the object on the basis of detection results of the terahertz wave detection portion.

17. A terahertz wave generation device comprising:
a light pulse generation device that generates a light pulse; and
the photoconductive antenna according to claim 1 which generates the terahertz wave by irradiation with the light pulse.

18. A camera comprising:
a light pulse generation device that generates a light pulse;
the photoconductive antenna according to claim 1 which generates the terahertz wave by irradiation with the light pulse;
a terahertz wave detection portion that detects the terahertz wave emitted from the photoconductive antenna and passing through an object or the terahertz wave reflected from the object; and
a storage portion that stores detection results of the terahertz wave detection portion.

19. An imaging device comprising:
a light pulse generation device that generates a light pulse;
the photoconductive antenna according to claim 1 which generates the terahertz wave by irradiation with the light pulse;
a terahertz wave detection portion that detects the terahertz wave emitted from the photoconductive antenna and passing through an object or the terahertz wave reflected from the object; and
an image forming portion that generates an image of the object on the basis of detection results of the terahertz wave detection portion.

20. A measurement device comprising:
a light pulse generation device that generates a light pulse;
the photoconductive antenna according to claim 1 which generates the terahertz wave by irradiation with the light pulse;
a terahertz wave detection portion that detects the terahertz wave emitted from the photoconductive antenna and passing through an object or the terahertz wave reflected from the object; and a measurement portion that measures the object on the basis of detection results of the terahertz wave detection portion.

* * * * *